(12) United States Patent
Mentak

(10) Patent No.: US 8,216,629 B2
(45) Date of Patent: Jul. 10, 2012

(54) LUBRICIOUS INTRAOCULAR LENS INSERTION DEVICE

(75) Inventor: Khalid Mentak, San Ramon, CA (US)

(73) Assignee: Advanced Vision Science, Inc., Goleta, CA (US)

( * ) Notice: Subject to any disclaimer, the term of this patent is extended or adjusted under 35 U.S.C. 154(b) by 1195 days.

(21) Appl. No.: 11/980,070

(22) Filed: Oct. 29, 2007

(65) Prior Publication Data

US 2009/0112313 A1    Apr. 30, 2009

(51) Int. Cl.
*B05D 3/02* (2006.01)
*A61F 9/00* (2006.01)
*A61F 2/16* (2006.01)

(52) U.S. Cl. .... 427/2.1; 427/2.24; 427/2.25; 427/372.2; 606/107; 623/6.11

(58) Field of Classification Search .................... 427/2.1, 427/2.24, 2.25; 606/107; 623/6.11
See application file for complete search history.

(56) References Cited

U.S. PATENT DOCUMENTS

| | | | |
|---|---|---|---|
| 5,331,027 A * | 7/1994 | Whitbourne | 524/37 |
| 5,803,925 A * | 9/1998 | Yang et al. | 606/107 |
| 6,083,230 A | 7/2000 | Makker et al. | |
| 6,270,902 B1 * | 8/2001 | Tedeschi et al. | 428/423.1 |
| 6,656,517 B2 * | 12/2003 | Michal et al. | 427/2.24 |
| 2003/0008153 A1 * | 1/2003 | Migliorini et al. | 428/447 |
| 2004/0121037 A1 * | 6/2004 | Rouns et al. | 425/515 |
| 2004/0151930 A1 | 8/2004 | Rouns et al. | |
| 2005/0064176 A1 | 3/2005 | Terry | |
| 2005/0256528 A1 * | 11/2005 | Beavers et al. | 606/107 |

FOREIGN PATENT DOCUMENTS

| | | |
|---|---|---|
| WO | WO 96/23600 | 8/1996 |
| WO | WO 2005/062965 | 7/2005 |

OTHER PUBLICATIONS

Rigacci et al. "Preparation of polyurethane based aerogels and xerogels for thermal superinsulation" Journal of Non-Crystalline Solids vol. 350. Dec. 2004. pp. 372-378.*
International Search Report for PCT/US2008/080542, mailed May 15, 2009, 20 pgs.

* cited by examiner

*Primary Examiner* — Timothy Meeks
*Assistant Examiner* — Cachet Sellman
(74) *Attorney, Agent, or Firm* — Squire Sanders (US) LLP

(57) ABSTRACT

This invention relates to a method of making an intraocular lens insertion device comprising a lubricious insertion tip assembly and to the device itself.

22 Claims, 1 Drawing Sheet

LUBRICIOUS INTRAOCULAR LENS INSERTION DEVICE

BACKGROUND

The human eye is susceptible to numerous conditions that can deleteriously affect the crystalline lens. Certain diseases and disorders may also directly or collaterally cause damage to the natural lens of the eye thereby resulting is impaired vision and even blindness. Cataracts, for example, are opaque growths in the cornea that can arise as complication of diseases such as diabetes. Cataracts can also arise simply due to the effects of aging. Fortunately, modern medical science is capable of assuaging the most severe consequences of lens damage and providing patients suffering from such with a renewed outlook on life. The procedure for accomplishing this is surgical removal of the damaged natural lens and its replacement with a polymeric artificial lens referred to as an intraocular lens or IOL.

An IOL can be implanted in the eye as a total replacement for a damaged natural lens, as would most often be the case with cataract surgery or it may be implanted to provide vision correction in an eye in which the natural lens is still functioning.

Generally, IOLs comprise a disk-like optic, which is the portion of the IOL that actually replaces or augments the function of the natural lens, and any number of flexible members or haptics that extend radially outward from the optic and affix themselves securely to portions of the eye to secure the position of the optic. Implantation of IOLs into the eye involves making a surgical incision in the eye which it preferably as small as possible to reduce trauma and speed healing.

Early generation IOLs were constructed of rigid biocompatible polymers such as poly(methyl methacrylate)s. These lenses required relatively large and therefore undesirable incisions in the eye to insert them through. To deal with this problem, IOLs were subsequently developed that were deformable, i.e., flexible. Exemplary deformable IOLs are those made of silicone polymers and hydrogels. The deformable IOLs can be rolled into tubes or folded into various configurations, all of which present a substantially reduced profile for insertion into an eye. Incisions as small as 1-3 mm are common when such deformable lenses are used.

Numerous devices have been created and many others are proposed to aid in the insertion of the rolled/folded IOL into an eye. In one current manifestation, the IOL is first folded into a shape resembling a taco and then is pushed through an insertion cartridge or "insertion tip" whereby it is progressively rolled into a tubular shape in which conformation it can be readily inserted into an eye through a miniscule incision such as that mentioned above. Due, however, to the nature of the polymers used for the deformable IOLs and those used for the insertion device, significant frictional forces often arose between the rolled IOL and the polymer of the insertion tip. This friction too often could result in damage to the IOL, even to the point of rendering it unusable, in which case the procedure had to be repeated.

What is needed is an insertion cartridge or tip that is more lubricious than those currently in use so as to facilitate the transfer of the IOL from the insertion device into the eye. The present invention provides such a lubricious device.

SUMMARY OF THE INVENTION

Thus, in one aspect the current invention relates to a method comprising providing an intraocular lens insertion device having a polymeric insertion tip assembly, contacting the insertion tip assembly with a polymeric primer dissolved in a first solvent, removing the insertion tip assembly from contact with the primer/first solvent to form a primed insertion tip, drying the primed insertion tip assembly, curing the primed and dried insertion tip assembly, contacting the primed, dried and cured insertion tip assembly with a lubricious polymer dissolved in a second solvent or solvent system having a Hildebrand solubility parameter that is from about 0.5 $(cal/cc)^{1/2}$ to about 2.5 $(cal/cc)^{1/2}$ greater than the Hildebrand solubility parameter of the insertion tip assembly polymer, removing the primed, dried and cured insertion tip assembly from the lubricious polymer/second solvent to form a lubricious insertion tip assembly, drying the lubricious insertion tip assembly and curing the lubricious insertion tip assembly.

In an aspect of this invention, the primer polymer is dissolved in the first solvent at a concentration from about 0.1% to about 10%.

In an aspect of this invention, the primer polymer is dissolved in the first solvent at a concentration from about 0.25% to about 1.0%.

In an aspect of this invention, the insertion tip assembly is contacted with the primer/first solvent at about 20° C. to about 100° C. for about 30 seconds to about 24 hours.

In an aspect of this invention, the primed insertion tip assembly is dried at ambient temperature for about 5 minutes to about 12 hours.

In an aspect of this invention, the primed and dried insertion tip assembly is cured at about 30° C. to about 110° C. for about 5 minutes to about 12 hours.

In an aspect of this invention, the lubricious polymer is dissolved in the second solvent at a concentration of about 0.1% to about 50%.

In an aspect of this invention, the primed, dried and cured insertion tip assembly is contacted with the lubricious polymer/second solvent at about 20° C. to about 100° C. for about 30 seconds to about 24 hours.

In an aspect of this invention, the lubricious insertion tip is dried at ambient temperature for about 5 minutes to about 12 hours.

In an aspect of this invention, the dried lubricious insertion tip is cured at about 30° C. to about 110° C. for about 5 minutes to about 12 hours.

In an aspect of this invention, the insertion tip assembly comprises polypropylene.

In an aspect of this invention, the primer comprises a polypropylene copolymer.

In an aspect of this invention, the polypropylene copolymer is poly(propylene-graft-maleic anhydride).

In an aspect of this invention, the first solvent is selected from the group consisting of tetrahydrofuran, 50:50 isopropanol/water; 70:30 ethanol:chloroform and 60:30 water/tetrahydrofuran.

In an aspect of this invention, the primer is dissolved in the first solvent at a concentration from about 0.4% to about 0.6%.

In an aspect of this invention, the insertion tip assembly is contacted with the primer/first solvent at a temperature of about 20° C. to about 40° C. for about 15 seconds to about 2 minutes.

In an aspect of this invention, the primed insertion tip assembly is dried at ambient temperature from about 1 to about 4 hours.

In an aspect of this invention, the primed and dried insertion tip assembly is cured at about 80° C. to about 90° C. for about 2 to about 4 hours.

In an aspect of this invention, the lubricious polymer is selected from the group consisting of HYDROMED 640™, HYDROSLIP C™, polyvinylpyrrolidone, poly(hydroxyethylmethacryate), poly(hydroxypropylmethylcellosolve), poly(hydroxyproplymethylcellulose) and hyaluronic acid.

In an aspect of this invention, the second solvent is selected from the group consisting of carbon tetrachloride, xylene, ethyl acetate, toluene, tetrahydrofuran, benzene, chloroform, trichloroethylene, cellosolve acetate, methyl ethyl ketone, acetone, diacetone alcohol, ethylene chloride, methylene chloride, butyl cellosolve pyridine and morpholine.

In an aspect of this invention, the lubricious polymer is dissolved in the second solvent at a concentration from about 0.5% to about 5%.

In an aspect of this invention, the primed, dried and cured insertion tip is contacted with the lubricious polymer/second solvent at about 20° C. to about 40° C. for about 15 seconds to about 5 minutes.

In an aspect of this invention, the lubricious insertion tip is dried at ambient temperature for about 1 hour to about 3 hours.

In an aspect of this invention, the dried lubricious insertion tip is cured at about 80° C. to about 90° C. for about 1 hour to about 3 hours.

An aspect of this invention is a lubricious insertion tip made by the method of claim 1.

DETAILED DESCRIPTION

Brief Description of the Drawings

The figures are presented solely as an aid in understanding the present invention. They are not intended nor should they be construed as limiting the scope of this invention in any manner whatsoever.

DISCUSSION

Use of the singular herein includes the plural and visa versa unless expressly stated to be otherwise. That is, "a" and "the" is to be construed as referring to one or more of whatever the word modifies. As a non-limiting example, "a lubricious polymer" includes one such polymer, two such agents or, under the right circumstances, more such polymers unless it is expressly stated or is unambiguously obvious from the context that such is not intended. Likewise, "a solvent" may refer to a single solvent or a mixture of two or more solvents unless, again, it is expressly stated or obvious from the context that such is not intended.

As used herein, words of approximation such as, without limitation, "about" "substantially," "essentially" and "approximately" mean that the feature that is noted as being "about," "substantially" and the like need not be exactly that which is expressly set forth in claim but may vary to some extent. The extent to which the feature may vary will depend on how great a change can be incorporated into the feature and have one of ordinary skill in the art still recognize the modified feature as having the characteristics and capabilities of the feature unmodified. In general, but subject to the preceding discussion, a numerical value herein that is modified by a word of approximation such as "about" may vary from the stated value by at least ±10%. Thus, for instance, "about 30° C." means a range of at least 27° C. to 33° C.

As used herein an "intraocular lens insertion device" (ILID) refers to a device designed to facilitate the insertion of a foldable intraocular lens (FIOL) through a very small—1 mm to 3 mm—incision in an eye after which the lens unfolds to become an artificial lens replacing the natural cornea which for some reason had to be removed. Virtually all ILIDs comprise an injector tip, the portion of the device that actually enters the eye and through which the FIOL is inserted into the space previously occupied by the natural lens. The injector tip may be integral with the body of the ILID or it may be separable from the main body of the ILID. Either type of injector tip will be amenable to the method of this invention. If the injector tip is integral to the body of the ILID, then the end of the ILID that comprises the injector tip will be subject to the method of this invention. If the injector tip is separable from the body of the ILID, then it may be disconnected, separately subjected to the method of this invention, and then reassembled with the body of the ILID.

Figure 1A:
FIG. 1A shows a representative intraocular lens insertion device.
Figure 1B:
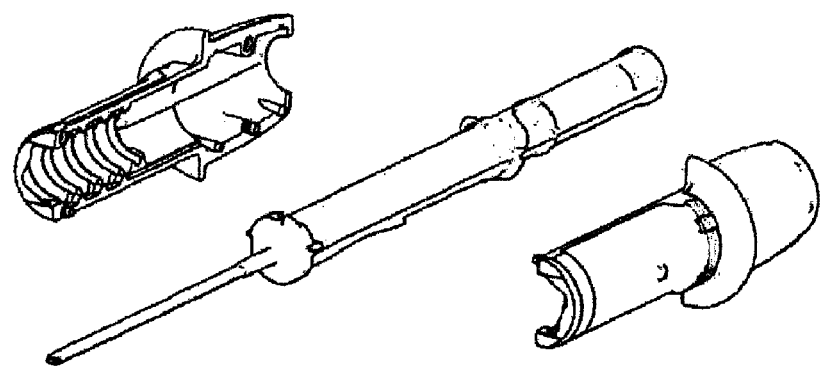
FIG. 1B shows a blow-up of the intraocular lens insertion device of FIG. 1A.
Figure 1B:
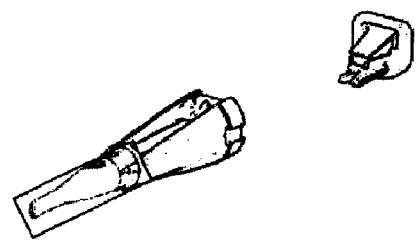
Figure 1B:
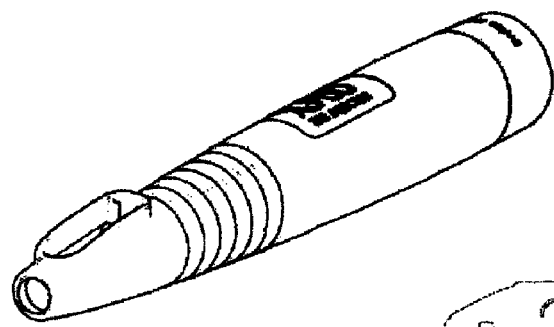
Figure 1B:
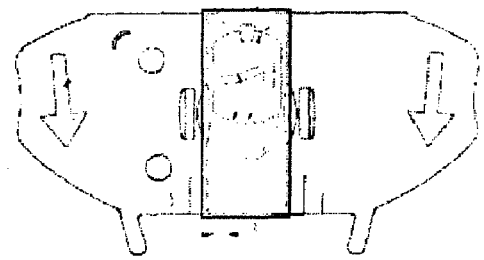

A representative (ILID) 10 is shown in FIG. 1. FIG. 1A shows the fully assembled device while FIG. 1B shows the device disassembled to reveal its various parts. As noted above, the critical element of the device for the purposes of this invention is the tip assembly 15 in which a FIOL would be situated prior to insertion into the eye of a patient and through which the FIOL must pass to get into the eye. It is the tip assembly that is coated with the lubricious polymer of this invention. It is emphasized that the ILID and tip assembly shown in FIG. 1 is provided for discussion purposes only and is not intended nor should it be construed as limiting the scope of this invention in any manner. There are a number of ILID designs currently in use, many others are disclosed in the literature, and it is likely that more will appear as time passes. Any such ILID will be amenable to the method herein so long as it comprises a polymeric tip assembly that is inserted into the intraocular space of a patient's eye and through which a folded intraocular lens is passed into the space where it unfolds and becomes the patient's new lens. Thus, so long as the surfaces that come in contact with an FIOL to be inserted into a patient's eye comprise polymers, they will be amenable to the method of this invention and all such injectors, whether currently known or as may be disclosed in the future will benefit from the lubricious coating of the method herein.

As used herein, "tip," "insertion tip," "tip assembly" and "insertion tip assembly" are used interchangeably to refer to all parts of an ILID that, when the ILID is in use to inject a FIOL into a patient's eye, at any time come in contact with the FIOL. It may also further refer to any part of an ILID that comes in contact with a any part of a patient's eye whether or not that part of the ILID comes in contact with an FIOL. That is, while it is an aspect of this invention to lubricate the interior portions of the tip assembly that will come in contact with an FIOL and thereby to reduce friction between the tip assembly polymer and the FIOL polymer, it is understood that the outer surface of the portion of the tip that is inserted into the eye will also benefit from a coating of a lubricious polymer of this invention to ease its insertion into and removal from the eye.

"When the tip is in use" refers to any time from the time that the FIOL is loaded into the ILID, be it just prior to performance of the procedure or be it as the result of a pre-loading procedure performed at a time well prior to the time of the actual procedure through and including the time the tip is actually inserted into the eye of a patient, the FIOL is ejected through the tip into the inner eye and the tip is finally retracted from the eye.

As used herein a "polymeric primer" refers to a polymer or blend of polymers that exhibit good adhesion characteristics with regard to the polymer comprising the insertion tip and good adhesion characteristics with regard to the lubricious polymer. Thus, a primer layer serves as an adhesion-enhancing intermediary between the insertion tip polymer and the lubricious polymer. It is presently preferred that the primer be a copolymer in which at least one of the constitutional units is compatible with the tip polymer and at least one constitutional unit is compatible with the lubricious polymer. A "constitutional unit" refers to a repeating unit as it appears in the copolymer after the monomer from which it is derived has reacted to form the polymer. For example, polypropylene comprises the constitutional unit —$CH_2CH(CH_3)$— which is derived from the monomer $CH_2$=$C(CH_3)$.

"Contacting" an ILID tip assembly with a primer/first solvent means that at least all surfaces of a tip assembly that will at any time contact an FIOL when the device is in use are put in intimate, continuous contact with a solution of the primer in a solvent for a requisite time at an indicated temperature. The time and temperature will easily be empirically determined based on the disclosure herein and simply refers to that time and temperature that provides a robust lubricious coating on the insertion tip without any detriment to the overall structure of the insertion tip.

As used herein, a first solvent refers to any solvent that fully dissolves the primer polymer and that preferably but not necessarily is capable of causing the tip assembly polymer to swell such that the primer polymer and the tip assembly polymer interact intimately to create a more robust interface than if a solvent that is not capable of swelling the tip assembly polymer were used. For the purposes of this invention, however, so long as the solution of the first polymer is capable of wetting the insertion tip polymer sufficiently to allow the formation of a uniform primer layer, any solvent that will accomplish this purpose may be used.

The primer polymer is dissolved in the first solvent at a relatively low concentration, i.e., from about 0.1% to about 10%, preferable at present from about 0.25% to about 1.0%.

The primer is applied to the injector tip by any means known in the art. The simplest and currently preferred means is simply to submerge the insertion tip in the polymer/first solvent solution. The injector tip may be left in contact with the primer/first solvent for a relatively expansive range of time, i.e., from about 30 seconds to about 24 hours. It will be appreciated that the exact time within these ranges will be readily ascertainable by those of ordinary skill in the art based on the disclosures here.

It is likewise possible to subject the insertion tip to the primer/first solvent over a relatively broad range of temperatures, i.e., from about 20° C. to about 100° C., again, based on the particular polymer the insertion tip assembly is made or and the nature of the primer polymer.

After the primer has been applied to the injector tip, the solvent is removed by drying under relatively mild conditions, preferably at present at about ambient temperature, that is, the environmental temperature of the area in which the tip is located, often referred to simply as room temperature, for virtually any desired period of time over a minimum amount to make sure the primer dry, i.e., generally from about 5 minutes to about 12 hours.

Once the primer layer has been dried, it is cured at a higher temperature, that is, from about 30° C. to about 110° C. for about 5 minutes to about 12 hours. As above, the exact time will be easily determined by those skilled in the art based on the disclosures herein.

The cured primed insertion tip is then contacted with a lubricious polymer that is dissolved in a second solvent. The second solvent is selected such that it is capable of dissolving the lubricious polymer and, when the lubricious polymer solution is contacted with the tip assembly, causing the tip assembly polymer to swell such that for the lubricious polymer and the tip assembly polymer compatible portions of the primer polymer may physically interact with the swollen tip assembly polymer to create a robust adhesion layer of primer and lubricious polymer on the tip assembly. To accomplish this it is presently preferred that the second solvent or mixture of solvents have a Hildebrand solubility parameter (HSP) of from about 0.5 to about 2.5 $(cal/cc)^{1/2}$ higher than that of the tip assembly polymer. This will insure that the tip assembly polymer swells but does not dissolve and that the structure of the tip assembly is not damaged in the process.

While it is possible to empirically identify applicable solvents that satisfy the preceding two criteria, a presently preferred means of identifying such solvents is to compare their intrinsic solubility parameter of the solvent to that of the tip assembly polymer. While there are numerous measures of intrinsic solubility parameter, it is presently preferred to use the Hildebrand solubility parameter, $\delta$, as the basis for comparing the solvents and polymers for the purposes of this invention. It is understood, however that any measure of intrinsic solubility may be used so long as the values attached to solvents and polymers in the selected measure directly relate to the values of the Hildebrand values provided herein.

The Hildebrand solubility parameter (HSP) is a measure of the compatibility of non-ionic non-aqueous solvents and by extension polymers and gives a numerical value to the rule-of-thumb that "like dissolves like." That is, solvents that have similar $\delta$ values are more likely to be compatible or miscible than solvents with widely disparate $\delta$ values and, further, a polymer with an HSP close to that of a solvent or solvent system will very likely be soluble in that solvent or solvent system. Further, the value of the HSP is also a measure of "solvent strength," that is, how powerful a solvent a particular liquid is. Some HSP values are shown in Table 1. Others may be found in the literature or may be empirically determined by procedures well-known to those skilled in the art.

TABLE 1

| Solvent | $\delta$ |
|---|---|
| n-Pentane | (7.0) |
| n-Hexane | 7.24 |
| Freon ® TF | 7.25 |
| n-Heptane | (7.4) |
| Diethyl ether | 7.62 |
| 1,1,1 Trichloroethane | 8.57 |
| n-Dodecane | |
| White spirit | |
| Turpentine | |
| Cyclohexane | 8.18 |
| Amyl acetate | (8.5) |
| Carbon tetrachloride | 8.65 |
| Xylene | 8.85 |
| Ethyl acetate | 9.10 |
| Toluene | 8.91 |
| Tetrahydrofuran | 9.52 |
| Benzene | 9.15 |
| Chloroform | 9.21 |
| Trichloroethylene | 9.28 |
| Cellosolve ® acetate | 9.60 |
| Methyl ethyl ketone | 9.27 |
| Acetone | 9.77 |
| Diacetone alcohol | 10.18 |
| Ethylene dichloride | 9.76 |
| Methylene chloride | 9.93 |
| Butyl Cellosolve ® | 10.24 |
| Pyridine | 10.61 |
| Cellosolve ® | 11.88 |
| Morpholine | 10.52 |

TABLE 1-continued

| Solvent | δ |
|---|---|
| Dimethylformamide | 12.14 |
| n-Propyl alcohol | 11.97 |
| Ethyl alcohol | 12.92 |
| Dimethyl sulphoxide | 12.93 |
| n-Butyl alcohol | 11.30 |
| Methyl alcohol | 14.28 |
| Propylene glycol | 14.80 |
| Ethylene glycol | 16.30 |
| Glycerol | 21.10 |
| Water | 23.5 |

HSPs are somewhat unique in that the HSP of solvent mixtures (or "solvent system" which is used herein simply to refer to mixtures of solvents) can be easily derived by simply adding the values of each solvent's HSP adjusted according to its percent of the total mixture. For example a mixture of two parts toluene and one part acetone would have an HSP of 9.10, that is: (8.91(0.66)+9.77(0.33)). Thus systems of solvents contemplated by this invention and those skilled in the art will be able to easily determine what mixtures should work with a particular polymer.

While the method of this invention is general and will be useful for increasing the lubricity of ILID tips made of any polymer, at present a preferred polymer in the industry for use as tip assemblies is polypropylene. Polypropylene has a HSP of approximately 8.1. Thus the presently preferred solvent or mixture of solvents that is capable of swelling polypropylene as required by the method herein should have a HSP of from about 8.6 to about 10.6.

As used herein a lubricious polymer is one that when applied to a surface and then exposed to an aqueous environment causes the surface to become slipperier than it would be if the lubricious polymer was not on the surface. Other surfaces, such as an FIOL, that come in contact with the lubricious polymer coating will tend to move over the treated surface more easily and with less, preferably no, damaging abrasive contact resulting from frictional forces between the surfaces. Lubricious polymers useful in the method of this invention include naturally-occurring polymers, semi-synthetic polymers and synthetic polymers. Semi-synthetic polymers refer to naturally-occurring polymers that have been chemically modified in the laboratory. Synthetic polymers are those that are completely man-made. Examples of naturally-occurring polymers that may be used in the method of this invention include, without limitation polysaccharides, cellulose, dextran and hyaluronic acid. Examples of semi-synthetic polymers that may be used in the method of this invention include, without limitation methyl cellulose, ethyl cellulose, carboxymethyl cellulose, hydroxypropyl cellulose and the like. Lubricious synthetic polymer that may be used in the method of this invention include, again without limitation, polyalkylene glycols, poly(vinylpyrrolidone), poly(N-alkylacrylamide, poly(acrylic acid), poly(vinyl alcohol), poly(ethyleneimine), polyamides, poly(vinyl sulfonic acid) and polyurethanes.

It is particularly preferred at present that the lubricious polymer be a hydrogel. When hydrated and placed in an aqueous environment, such as that inside the cornea, the high water content of the hydrogel provides a very lubricious surface for the FIOL to traverse. Many of the polymers mentioned above are either inherently hydrogels of can be rendered hydrogel-like by light cross-linking. Techniques for creating hydrogels are well-known to those skilled in the art. A presently preferred hydrogel for use with polypropylene tip assemblies is poly(propylene-graft-maleic anhydride).

Without being held to any particular theory, it is presently believed that the physical interspersion of the primer and lubricious polymer chains with the tip assembly polymer results in a robust, well-adhered coating without formation of a formal interpenetrating polymer network (IPN) or even a semi- or pseudo-IPN. A formal IPN requires that the polymer strands be intertwined in such a manner that only the breaking of chemical bonds will result in the strand separation. This is accomplished by cross-linking both of the polymers. For semi- or pseudo-IPNs, only one of the two polymers is cross-linked meaning that, while difficult, the polymer strands can be separated without breaking chemical bonds. Semi-/pseudo-IPNs are formed by preparing one polymer, cross-linking it and then permeating it with the monomer(s) that will become the second polymer. It is also possible to form a first uncross-linked polymer and permeate it with a monomer that affords a polymer that is capable of being cross-linked. While full, semi- or pseudo-IPNs might find use in the formation of lubricious ILID tip assemblies, the method of synthesizing them engenders several problems when dealing with an end product designed to be placed in the eye. Primarily, the preparation of IPNs or semi- or pseudo-IPNs requires at least one monomeric material. Often, if not in fact usually, such monomers are not biocompatible, particularly not in the eye, and therefore great care must be taken to completely remove any unreacted monomer from the final lubricious coating, which may or may not be possible. The current invention, while providing a robust lubricious coating that rivals that which could be produced using IPNs, avoids completely this difficulty in that all polymers used in the method, the polymer of the ILID tip assembly of course but more importantly the primer polymer and the lubricious polymer are pre-purified so that the composition of each polymer is fully characterized prior to its being incorporated in the method of this invention.

As might be expected, under most circumstances the lubricious polymer and the tip assembly polymer are vastly different in composition and physical characteristics. Thus, a primer, which as noted above has constitutional units compatible with the top assembly polymer and constitutional units compatible with the lubricious polymer, is a presently preferred embodiment of this invention. A non-limiting example of this would be the use of a polypropylene-containing copolymer primer for use with a polypropylene tip assembly in which the copolymer also comprises a relatively hydrophilic constitutional unit. A non-limiting example of such a copolymer for use when the tip assembly polymer is polypropylene is polypropylene-graft-maleic anhydride, chlorinated. Polypropylene-graft-maleic anhydride, chlorinated, is a readily available commercial product. In the graft copolymer, the polypropylene backbone is, of course, compatible with the polypropylene of the tip assembly and will tend to more intimately intersperse with the swollen tip assembly polymer. Maleic anhydride on the other hand can hydrolyze to maleic acid with the resulting two carboxylic acid moieties providing substantial hydrophilicity and therefore enhanced compatibility with the hydrophilic lubricious polymer, which should result in greater intertwining of the hydrophilic portions of the polymer strands.

A non-limiting exemplary general procedure for implementing this invention with the insertion tip assembly polymer is polypropylene comprises the following: first, if desired, the ILID tips can be cleaned to remove surface contaminants. Standard cleaning solvents such as alcohols (e.g. ethanol) may be used. A primer polymer is then dissolved in an appropriate solvent selected as described above at a concentration of about 0.25% to about 1.5%, preferably at present from about 0.4% to about 0.6. The temperature of the solution is adjusted to about 20° C. to about 40° C. and the (cleaned) tip assembly is submerged in the solution for about 15 seconds to about 10 minutes, preferably at present about 15 seconds to about 2 minutes. The tips are then removed from the solution and dried at ambient temperature, about 20° C. to about 40° C. for from about 1 minutes to about 4 hours. When dry, the tips are cured at a temperature of about 60° C. to about 110° C., preferably at present from about 80° C. to about 100° C. for about 1 hour to about 4 hours. The dried tip assembly is then submerged in a solution of the lubricious polymer, which is at a concentration from about 0.5% to about 5.0% in a solvent that has an HSP of about 0.5 to about 2.5 (cal/cc)$^{1/2}$ greater than that of the tip assembly polymer, at a temperature from about 20° C. to about 80° C., preferably at present from about 40° C. to about 50° C. Once the ILID tip has been in the lubricious polymer solution for the requisite time, it is removed and air dried at ambient temperature for from about 1 hour to about 3 hours. It is then cured at about 30° C. to about 110° C., preferably about 80° C. to about 90° C. for about 1 hour to about 3 hours.

Again, exact times and temperatures will be easily determinable without undue experimentation by those skilled in the art based on knowledge of the disclosures herein. Also, as mentioned previously, any means of contacting the tip assembly with the lubricious polymer solution is within the scope of this invention; preferred at present is simply to submerge the tip assembly in the lubricious polymer solution.

EXAMPLES

Example 1

Ten polypropylene tip assemblies were placed in a 200 ml glass beaker containing 100 ml of ethanol. A Teflon-coated bar magnet was placed in the solution and the solution was stirred using a magnetic stirrer for 10 minutes at room temperature to remove surface contaminants. The tip assemblies were then removed from the ethanol, placed on a Teflon sheet and dried in an oven at 60° C. for 6 hours.

Polypropylene-graft-maleic anhydride, chlorinated, primer was dissolved in tetrahydrofuran (THF) at a concentration of 0.5%. The THF can be heated if necessary to assist in dissolution of the polymer but once the polymer is dissolved, the solution is allowed to cool to ambient (room) temperature before the next step.

The dried tips were then submerged in the primer solution for 45 seconds, removed, air dried at room temperature for two hours and then oven cured at 85° C. for an additional two hours.

Meanwhile, HYDROMED 640™, a commercial polyurethane hydrogel, was dissolved in THF at a concentration of 1.5%.

The primed tip assemblies were then submerged in the hydrogel/THF solution for one minute, removed, allowed to dry at room temperature for two hours and then placed in a 85° C. oven for an additional two hours. The oven was turned off and the tips were allowed to cool to room temperature while still in the oven.

Example 2

The above procedure was followed except that unprimed tip assemblies were used and the HYDROMED 640 was dissolved in a variety of solvents with different HSPs. IOLs were placed in the coated tip assemblies and the tips were reattached to an ILID body. The force required to eject the IOL from the tip assembly was measured as was the condition of the polymer coating after IOL ejection. The results are shown in Table 2.

TABLE 2

| Solvent | δ (cal/cc)$^{1/2}$ | Force (Newtons, N) | Delamination |
|---|---|---|---|
| Diethyl ether | 7.62 | Lens could not be injected | extensive |
| Cyclohexane | 8.18 | Lens could not be injected | moderate |
| Xylene | 8.85 | 21.75 | moderate |
| Toluene | 8.91 | 17.40 | slight |
| Tetrahydrofuran | 9.52 | 6.22 | No |
| Benzene | 9.15 | 6.48 | No |
| Chloroform | 9.21 | 6.93 | No |
| Trichloroethylene | 9.28 | 7.68 | No |
| Acetone | 9.77 | 8.10 | No |
| Methylene chloride | 9.93 | 12.53 | slight |
| Pyridine | 10.61 | 14.10 | slight |
| n-Propyl alcohol | 11.97 | 18.30 | Moderate |
| Ethyl alcohol | 12.92 | Lens could not be injected | extensive |
| Methyl alcohol | 14.28 | Lens could not be injected | extensive |

Example 3

The same procedure as that described in Example 1 was followed using 0.2% HYDROSLIP C™ as the hydrogel instead of HYDROMED 640™.

Example 4

The same procedure as that described in Example 1 was followed using 1.0% polyvinylpyrrolidone (PVP-C15) as the hydrogel. The PVP-C15 was dissolved in 50:50 isopropanol:THF.

Example 5

The same procedure as that described in Example 1 was followed using 0.5% polyhydroxyethylmethacrylate (MW 5000) dissolved in 70:30 ethanol:chloroform as the hydrogel.

Example 6

The same procedure as that described in Example 1 was followed using 0.3% hydroxypropylmethylcellulose dissolved in 60:30 water:THF as the hydrogel instead of HYDROMED 640™.

Each of the examples provided ILID tip assemblies that exhibited excellent lubricity and durability when tested with IOLs using the technique of Example 2.

What is claimed:
1. A method, comprising:
providing an intraocular lens insertion device having a polypropylene insertion tip assembly;
contacting the insertion tip assembly with a polypropylene copolymer primer dissolved in a first solvent;
removing the insertion tip assembly from contact with the primer/first solvent to form a primed insertion tip;
drying the primed insertion tip assembly;
curing the primed and dried insertion tip assembly;
contacting the primed, dried and cured insertion tip assembly with a lubricious polymer dissolved in a second solvent or solvent system having a Hildebrand solubility parameter that is from about 0.5 (cal/cc)$^{1/2}$ to about 2.5

(cal/cc)$^{1/2}$ greater than the Hildebrand solubility parameter of the insertion tip assembly polymer;

removing the primed, dried and cured insertion tip assembly from the lubricious polymer/second solvent to form a lubricious insertion tip assembly;

drying the lubricious insertion tip assembly; and, curing the lubricious insertion tip assembly.

2. The method of claim 1, wherein the primer polymer is dissolved in the first solvent at a concentration from about 0.1 wt % to about 10 wt %.

3. The method of claim 2, wherein primer polymer is dissolved in the first solvent at a concentration from about 0.25 wt % to about 1.0 wt %.

4. The method of claim 1, wherein the insertion tip assembly is contacted with the primer/first solvent at about 20° C. to about 100° C. for about 30 seconds to about 24 hours.

5. The method of claim 1, wherein the primed insertion tip assembly is dried at ambient temperature for about 5 minutes to about 12 hours.

6. The method of claim 1, wherein the primed and dried insertion tip assembly is cured at about 30° C. to about 110° C. for about 5 minutes to about 12 hours.

7. The method of claim 1, wherein the lubricious polymer is dissolved in the second solvent at a concentration of about 0.1 wt % to 50 wt %.

8. The method of claim 1, wherein the primed, dried and cured insertion tip assembly is contacted with the lubricious polymer/second solvent at about 20° C. to about 100° C. for about 30 seconds to about 24 hours.

9. The method of claim 1, wherein the lubricious insertion tip is dried at ambient temperature for about 5 minutes to about 12 hours.

10. The method of claim 1, wherein the dried lubricious insertion tip is cured at about 30° C. to about 110° C. for about 5 minutes to about 12 hours.

11. The method of claim 1, wherein the polypropylene copolymer is poly(propylene-graft-maleic anhydride).

12. The method of claim 11, wherein the first solvent is selected from the group consisting of tetrahydrofuran, 50:50 isopropanol/water; 70:30 ethanol:chloroform and 60:30 water/tetrahydrofuran.

13. The method of claim 12, wherein the primer is dissolved in the first solvent at a concentration from about 0.4 wt % to about 0.6 wt %.

14. The method of claim 13, wherein the insertion tip assembly is contacted with the primer/first solvent at a temperature of about 20° C. to about 40° C. for about 15 seconds to about 2 minutes.

15. The method of claim 14, wherein the primed insertion tip assembly is dried at ambient temperature from about 1 to about 4 hours.

16. The method of claim 15, wherein the primed and dried insertion tip assembly is cured at about 80° C. to about 90° C. for about 2 to about 4 hours.

17. The method of claim 16, wherein the lubricious polymer is selected from the group consisting of HYDROMED 640, HYDROSLIP C, polyvinylpyrrolidone, poly(hydroxyethylmethacryate), poly(hydroxypropylmethylcellosolve), poly(hydroxyproplymethylcellulose) and hyaluronic acid.

18. The method of claim 17, wherein the second solvent is selected from the group consisting of carbon tetrachloride, xylene, ethyl acetate, toluene, tetrahydrofuran, benzene, chloroform, trichloroethylene, cellosolve acetate, methyl ethyl ketone, acetone, diacetone alcohol, ethylene chloride, methylene chloride, butyl cellosolve pyridine and morpholine.

19. The method of claim 18, wherein the lubricious polymer is dissolved in the second solvent at a concentration from about 0.5 wt % to about 5 wt %.

20. The method of claim 19, wherein the primed, dried and cured insertion tip is contacted with the lubricious polymer/second solvent at about 20° C. to about 40° C. for about 15 seconds to about 5 minutes.

21. The method of claim 20, wherein the lubricious insertion tip is dried at ambient temperature for about 1 hour to about 3 hours.

22. The method of claim 21, wherein the dried lubricious insertion tip is cured at about 80° C. to about 90° C. for about 1 hour to about 3 hours.

* * * * *